(12) United States Patent
Baillet et al.

(10) Patent No.: US 11,464,723 B2
(45) Date of Patent: Oct. 11, 2022

(54) MOISTURIZING CREAM AND LOTION

(71) Applicant: Johnson & Johnson Consumer Inc., Skillman, NJ (US)

(72) Inventors: Hortense Baillet, Val de Reuil (FR); Marie Ceclie Geslin, Val de Reuil (FR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/411,553

(22) Filed: May 14, 2019

(65) Prior Publication Data
US 2019/0343743 A1 Nov. 14, 2019

Related U.S. Application Data

(60) Provisional application No. 62/671,044, filed on May 14, 2018.

(51) Int. Cl.
| | | |
|---|---|---|
| *A61K 8/37* | (2006.01) | |
| *A61K 8/34* | (2006.01) | |
| *A61K 8/55* | (2006.01) | |
| *A61K 8/58* | (2006.01) | |
| *A61K 8/72* | (2006.01) | |
| *A61K 8/81* | (2006.01) | |
| *A61Q 19/00* | (2006.01) | |
| *A61K 8/06* | (2006.01) | |

(52) U.S. Cl.
CPC ............ *A61K 8/375* (2013.01); *A61K 8/342* (2013.01); *A61K 8/55* (2013.01); *A61K 8/585* (2013.01); *A61K 8/72* (2013.01); *A61K 8/8147* (2013.01); *A61Q 19/00* (2013.01); *A61Q 19/007* (2013.01); *A61K 8/06* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 6,395,260 B1 | 5/2002 | Ley et al. | |
| 8,765,967 B2 | 7/2014 | Berg-Schultz | |
| 9,918,911 B2 | 3/2018 | Oreal | |
| 2008/0161418 A1* | 7/2008 | Dierker | A61K 8/31 514/762 |
| 2008/0292711 A1 | 11/2008 | Berg-Schultz | |
| 2010/0297044 A1 | 11/2010 | Bruening et al. | |
| 2013/0280197 A1* | 10/2013 | Geffroy | A61Q 19/001 424/64 |
| 2015/0190321 A1 | 7/2015 | Dierkier | |
| 2016/0206540 A1* | 7/2016 | Hood | A61K 8/4946 |
| 2017/0281527 A1* | 10/2017 | Ronen | A61K 8/19 |

FOREIGN PATENT DOCUMENTS

| | | |
|---|---|---|
| CA | 2607229 A1 | 11/2006 |
| EP | 2545901 B1 | 6/2012 |
| WO | WO 2005/053631 A1 | 6/2005 |

OTHER PUBLICATIONS

Trulux's product data sheet for Emulgade PL 68/50 obtained from the internet website, https://trulux.com.au/emulgade-pl-68-50/ (date unknown).*
BASF UL Prospectortr Product Datasheet obtained from the internet website, file:///C:/Users/slee2/Downloads/CUTINA_GMS_V.pdf (Year: 2015).*
International Search Report for PCT/IB2019/053983 dated Sep. 17, 2019.

* cited by examiner

Primary Examiner — Sin J Lee
(74) Attorney, Agent, or Firm — Laura A. Donnelly

(57) ABSTRACT

Personal care composition having superior moisturizing, slipperiness and evacuation rate properties are disclosed.

8 Claims, 2 Drawing Sheets

MOISTURIZING CREAM AND LOTION

This application claims priority of the benefits of the filing of U.S. Provisional Application Ser. No. 62/671,044, filed May 14, 2018, the contents of which are hereby incorporated by reference herein in their entirety.

FIELD OF THE INVENTION

The present invention is directed to a personal care composition having superior moisturizing, slipperiness and evacuation rate properties.

BACKGROUND OF THE INVENTION

Moisturizers are mixtures of chemical agents specially designed to make the external layers of the skin or hair softer. Personal care compositions having moisturizing properties are known. Consumers expect such compositions to satisfy a range of requirements. Apart from the skin/hair-care effects which determine the intended application, value is placed on such diverse parameters as dermatological compatibility, appearance, sensory impression, stability in storage and ease of use.

U.S. Patent Publication No. 20150190321 to Cognis discloses that a mixture consisting of mono- and dialkyl ethers of glycerol in a 1:1 to 1.3.1 ratio by weight has the emulsifying and consistency-imparting properties disclosed therein.

U.S. Patent Publication No. 20100297044 to Cognis discloses emulsifier mixtures that contain (a) 0.1 to 60% by weight of a fatty alcohol or fatty alcohol mixture, (b) 30 to 97% by weight of an ethoxylated fatty alcohol or mixture of ethoxylated fatty alcohols, (c) 0.1 to 20% by weight of a dialk(en)yl ether, a dialk(en)yl carbonate or a mixture of these components, and (d) less than 10% by weight of water.

U.S. Pat. No. 8,765,967 to DSM discloses sunscreen compositions that contain (i) cosmetic adjuvants and additives and (ii) microcapsules with UV filter activity made by a sol-gel method. The reference discloses that the sol-gel method includes emulsifying crosslinkable monomers, preferably silanes with and without UV filter activity, under high shear forces in an aqueous solution containing surfactants such as cetyltrimethylammonium chloride and the like and/or protective colloids such as PVP (polyvinylpyrolidon), PVA (polyvinyl alcohol) and the like that assist in stabilizing the emulsion.

U.S. Pat. No. 6,395,260 to Haarmann & Reimer GmbH discloses skin lightening compositions that contain benzaldoximes.

U.S. Patent Publication No. 20030171617 to Bayer discloses the use of 3,4-dihydroxymandelic acid alkylamides as antioxidants.

European Patent No. EP2545901B1 to Henkel discloses a skin care formulation that contains a polymer derived from at least one acid-containing monomer that is methacrylic acid and at least one N-alkyl (meth)acrylamide monomer, wherein the acid-containing monomer is present from 5 to 35 weight percent of the total monomer content in the polymer and wherein the N-alkyl (meth)acrylamide monomer is present from 27 to 88 percent of the total weight of the monomer content in the polymer; and at least one sunscreen active agent.

A need exists for personal care compositions that meet a range of consumers' needs.

SUMMARY OF THE INVENTION

The personal care composition according to the present invention contains the following ingredients:
an emollient, preferably cocoglyceride, from about >0% to about 10%, preferably from about 2% to about 6%; more preferably from about 3 to about 6%;
an emollient wax, preferably a cetyl alcohol, from about >0% to about 8%, preferably from about 1% to about 4%; more preferably from about 1.5% to about 3%;
an emulsifier, preferably a cetyl phosphate, from about 0.2% to about 1.4%, preferably from about 0.4% to about 1.4%; more preferably from about 0.5% to about 0.6%;
a gelling agent, preferably a carbomer, from about 0.4% to about 0.6%, preferably from about 0.4% to about 0.55%; and
from about 60% to about 90% water.

For clarity and to avoid any confusion between the "emollient" and the "emollient wax"; "emollient wax" is referred as to "wax" in many portions of the disclosure.

The ingredients are present in the personal care composition of the invention in the following ratios:
A) gelling agent/emulsifier: 1 to 0.5;
B) gelling agent/emollient: 1 to 0.02; and
C) wax/emollient: less than or equal to 0.5.

The personal care composition may be a lotion or a cream. A lotion is a low-viscosity topical preparation intended for application to the skin. By contrast, a cream has higher viscosity. A value of viscosity acceptable for the consumer ranges from 950 mPa 1600 mPas for lotions and 1400-4800 mPa for creams.

A lotion according to the present invention may contain the following ingredients:
an emollient, around 4%;
a emollient wax, around 2%;
an emulsifier, around 0.5%; and
a gelling agent, around 0.4%;

A cream according to the present invention may contain the following ingredients:
an emollient, around 6%;
a wax, around 3%;
an emulsifier, around 0.6%; and
a gelling agent, around 0.55%.

DETAILED DESCRIPTION OF THE INVENTION

Figure 1:
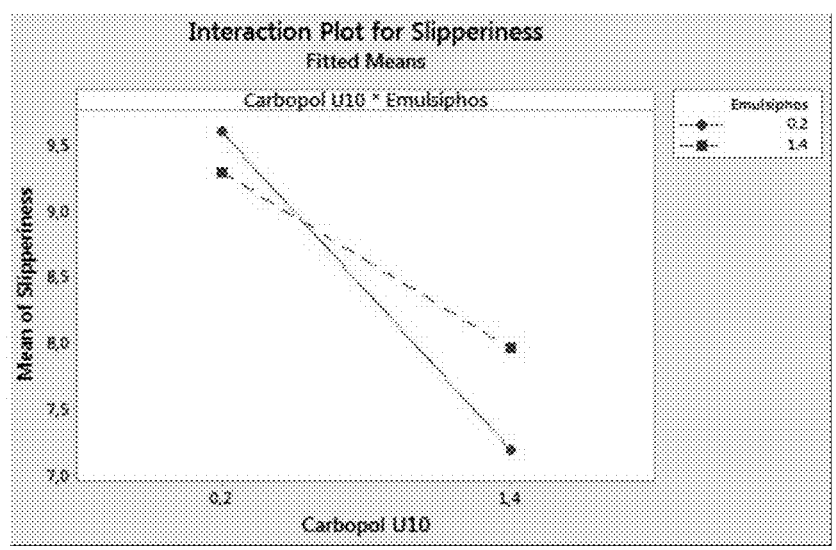
FIG. 1 is a graph showing slipperiness values relative to amount of gelling agent and amount of emulsifier.

Moisture can be held in the skin by applying a product to its surface that blocks water from leaving. Ingredients that help create a barrier on the surface of the skin include petrolatum, high concentrations of glycerin or other silicones, dimethicone, and mineral oil. Adding a barrier also helps provide an environment where dry skin more rapidly repairs itself and protects the skin from irritants or other harmful materials. Some moisturizing products contain synthetic biomemetic lipids that penetrate the stratum corneum and fill spaces where skin lipids are missing. These naturally derived synthetic lipids mimic skin lipids by attracting water into the skin and helping maintain the proper balance of oil and water in the skin.

Personal care compositions used to treat dry skin typically contain ingredients that compensate for dehydration by increasing the amount of water present in the stratum corneum. Such personal care compositions contain lipophilic moisturizing agents that inhibit water loss via occlusion. Suitable lipophilic moisturizing agents include polyols such as glycerol or glycols, or agents that protect the hydrolipid film of the skin by preventing evaporation of water by a barrier effect, including hydrocarbon substances such as liquid petroleum. However, the moisturization afforded by polyols is limited in time and barrier forming agents take time to build up. Humectants can also be used to increase moisture in the skin. Humectants are ingredients such as glycerin that attract, retain, and hold moisture from the air. Unfortunately, such moisturization techniques only lead to temporary relief from dry skin. More favorable techniques are those that repair and/or increase the skin barrier function, as these result in the skin feeling more moisturized for longer and benefit the health of the skin. Healthy skin barrier retains moisture and higher levels of hydration.

Scientifically, skin moisturization results from stimulation of epidermal differentiation and maturation of the stratum corneum. The keratinocyte proliferation in the basal layer, the innermost skin layer, differentiate gradually as they pass through the spinous layer and the granular layer. Through this keratinization process, the keratinocytes produce natural moisturizing factors (NMFs) and lipids (ceramides, cholesterols, and fatty acids), and form the stratum corneum, thereby contributing to a healthy skin barrier function and consequently hydrated skin, which is less prone to irritation and the effects of aging. Thus, keratinocyte differentiation can deliver skin moisturization and resistance to skin irritation, inflammation and/or ageing by providing the epidermis with the necessary cells and constituents to promote healthy skin barrier function and associated efficient water management. Therefore, means for inducing keratinocyte differentiation in epidermis would be highly desirable to counteract dehydration, dry skin conditions, effects of ageing and irritated and inflamed or otherwise sensitive skin.

One means of improving skin moisturization involves controlling the semi-permeability or moisture retaining capability of the skin by enhancing epidermal barrier function and renewal. The semi-permeability of the skin, in turn, plays a key role in skin moisturization and protection. However, external damage and/or intrinsic factors can affect this semi-permeability leading to dry and/or sensitive skin conditions. Therefore, in addition to delivering moisturization, one must also control the inflammatory and irritation processes that can occur to efficiently promote healthy skin barrier function, which in turn gives rise to healthy skin.

It is clear that the skin's internal or endogenous mechanism of maintaining moisturization is centered around optimal barrier function. The skin barrier function plays a key role in protecting the body against skin water loss and external aggression. An alteration of the skin barrier function increases trans-epidermal water loss and leads to dry and flaky skin, inflammation and injury.

A good moisturizer should (i) enhance keratinocyte differentiation to provide the skin with the necessary cells and constituents to increase the water content throughout the different layers of the skin of the epidermis and the stratum corneum, (ii) increase water transport, water channel proteins and natural moisturizing factors, which participate in promoting efficient water management and (iii) maintain an optimal skin lipid balance by increasing the synthesis of new lipids. The personal care composition of the present invention can provide such functions.

Definitions

Naturally occurring skin lipids and sterols, as well as artificial or natural oils, humectants, emollients, lubricants, etc., may be part of the composition of commercial personal care skin moisturizers.

An "emollient" is an additive that has the quality of softening or soothing the skin. Emollients are generally complex mixtures of chemical compounds that hold water in the skin after application and help smooth the skin. Emollients increase the skin's hydration (water content) by reducing evaporation. Preferred emollients are cocoglycerides, which are mixtures of mono, di and triglycerides derived from coconut oil.

An "emollient wax" or "wax" is an additive that (1) has the properties of an emollient; (2) is oil-based; (3) is solid at room temperature. A preferred emollient wax is cetyl alcohol, a fatty alcohol—palmitate/ester that is also known as hexadecan-1-ol or palmityl alcohol. Other examples include petrolatum and silicone-derived ingredients, such as cyclomethicone.

An "emulsifier" is an additive that stabilizes a mixture of two or more liquids that are normally immiscible. An example of an emulsifier is Emulsiphos®, a potassium salt of a complex mixture of esters of phosphoric acid and cetyl alcohol, available from Symrise GmbH & Co., Holzmiden, Germany.

A "gelling agent" is an additive that can form a polymer gelled composition by crosslinking or neutralization. Gelling agents can also stabilize emulsions, form gels, increase viscosity, etc. Examples of gelling agents include polyacrylate (such as carbomer) and polysaccharide (such as cellulose). A preferred gelling agent is carbomer, which is a polymeric chemical composed of acrylic acid monomers.

All percentages (%) are by weight unless otherwise specified herein.

In accordance with the present invention, specified amounts and ratios of ingredients are employed to impart desired properties to the personal care composition.

Amount of Ingredients

About the amount of the ingredients in the inventive compositions, the present inventors made the following observations:

Emollient (cocoglyceride). When from 0.1% to 2% of emollient was employed, the emollient effect was low. When from 2% to 6% of emollient was employed, good emollient properties were observed. When from 6% to 10% of emollient was employed, the composition exhibited an oily feeling.

Wax (cetyl alcohol). When from >0% to 1% of wax was employed, the composition exhibited low consistency (body). When from 1% to 4% of wax was employed, the composition exhibited good consistency (body). When from 4% to 8% of wax was employed, the composition exhibited even more consistency (body), but may crystallize depending on the fatty phase of the composition (see ratio C below).

Emulsifier (potassium cetyl phosphate). When from 0.2 to 0.4% of emulsifier was employed, a risk to destabilize the emulsion (and therefore the composition) was observed. When from 0.4 to 1.4% of emulsifier was employed, the composition exhibited good emulsion stability.

Gelling agent (carbomer). When from 0.2 to 0.3% of carbomer was employed, the composition was not viscous enough, too fluid. When from 0.3% to 0.6% of carbomer was employed, the composition had an average viscosity. When from 0.6 to 1.4% of carbomer was employed, the composition was highly viscous.

Ratio of Ingredients

About the ratio of the ingredients, the present inventors made the following observations:

Ratio A) Gelling Agent/Emulsifier: 1 to 0.5.

This ratio influences the slipperiness of the composition. "Slipperiness" means the degree to which a composition slides easily or causes something to slide because of being wet, smooth, or oily when applied onto the skin. It is preferable for the consumers to have a product with a slipperiness in a range of 6-9.5 as discussed in the examples below, particularly for the texture of hydration cream which will be applied on the skin and massaged to penetrate.

It has been observed that slipperiness can be controlled by the proportions and amounts of the gelling agent and the emulsifier. The slipperiness decreases while the amount of gelling agent increases. The slipperiness increases while the amount of emulsifier increases. It has been found that the best ratio to provide a desirable slipperiness while still allowing the ingredients to confer the composition their respective properties ranges from 1 to 0.5. This surprising effect was observed experimentally (see the examples below). The inventors have determined that the effect of the two ingredients on slipperiness is not the same and that at a certain point the effect of the gelling agent outweighs the effect of the emulsifier. To keep a satisfactory slipperiness, it was found that the ratio between the gelling agent and the emulsifier should range from 1 to 0.5.

Ratio B) Gelling Agent/Emollient: 1 to 0.02.

This ratio influences the evacuation rate of the composition. "Evacuation rate" means the amount of product that can be recovered from its packaging (for example a bottle with a pump). It is desirable for the consumer to have a product with an evacuation rate as high as possible, preferably above 82% for a lotion. In the case of a cream, the packaging is different (a jar for example) and the consumer has access to all of the product. It has been observed that this parameter can be controlled by the gelling agent and the emollient. The evacuation rate decreases while the amount of gelling agent increases. The evacuation rate decreases while the amount of emollient increases. It has been found that the best ratio to provide a desirable evacuation rate while still allowing the ingredients to confer the composition their respective properties ranges from 1 to 0.02. This surprising effect was observed experimentally (see the examples below).

Ratio C) Wax/Emollient: Inferior or Equal to 0.5.

This ratio influences the stability of the composition. Wax is important for the generation of a lamellar structure, but it also needs to be solubilized to prevent crystallization and destabilization of the composition. It has been found that the proper amount of emollient to solubilize the wax is at least 2 times the amount of wax used.

Additional Ingredients.

The personal care composition may also contain additional ingredients commonly employed in moisturizing compositions. For example, the composition may contain glycerin; preferably from about 5% to about 10%. The composition may also contain preservative (henoxyethanol; ethylhexylglycerin). The composition may also contain absorbent (*Zea mays* starch). The composition may also contain one or more diluents. Suitable diluents include water.

Comparative Examples

The compositions in Table 1, Table 2 and Table 3 were prepared as follows:

In the main vessel introduce water, disodium EDTA and Carbopol Ultrez 10.
Control good dispersion of Carbopol and then heat to 80° C.
Add Glycerin and control temperature (80° C.).
Add Emulsiphos 977660, Myritol 331 and Lanette16.
Control that the Emulsiphos is completely melted: 15 min emulsion phase at 80° C.
Neutralize with an aqueous solution of Sodium hydroxide, p-Anisic acid to a target pH=5.6.
Start cooling down to 35° C.
When temperature reaches 40° C., optionally add Euxyl PE9010 then Corn Starch.
Check the good dispersion of purity and pH. Adjust pH if needed with NaOH to pH=5.6.

Myritol 331 (Cocoglyceride) available from BASF.
Carbopol® Ultrez 10 (Carbomer) available from Lubrizol Advanced Materials, Inc., Cleveland, Ohio
Emulsiphos 977660 (Potassium Cetyl phosphate) available from Symrise GmbH & Co.
Lanette16 (Cetyl alcohol) available from BASF.
Euxyl PE9010 (Phenoxyethanol; Ethylhexylglycerin) available from Elton Chemicals S.A.

Measurements and observations were made on compositions in Example 1 to Example 16 as set forth in the description below.

TABLE 1

Comparative Examples 1-5

| EU INCI Name | Function | Comparative Example 1 | Comparative Example 2 | Comparative Example 3 | Comparative Example 4 | Comparative Example 5 |
| --- | --- | --- | --- | --- | --- | --- |
| Aqua | Vehicle | 69.512 | 78.312 | 87.512 | 78.312 | 67.112 |
| Carbomer (Carbopol ® U10) | gelling agent | 0.2 | 1.4 | 0.2 | 0.2 | 1.4 |
| Potassium Cetyl Phosphate; Palm Glycerides | Emulsifier Hydrogenated | 0.2 | 0.2 | 0.2 | 1.4 | 1.4 |
| Cetyl Alcohol | Emollient (Wax) | 8 | 8 | 0 | 8 | 8 |
| Cocoglycerides (Myritol ® 331) | Emollient | 10 | 0 | 0 | 0 | 10 |
| Glycerin | humectant | 10 | 10 | 10 | 10 | 10 |
| Disodium EDTA | Chelant | 0.15 | 0.15 | 0.15 | 0.15 | 0.15 |
| p-Anisic Acid | masking agent | 0.15 | 0.15 | 0.15 | 0.15 | 0.15 |
| Sodium Hydroxide | pH ajuster | 0.188 | 0.188 | 0.188 | 0.188 | 0.188 |
| Phenoxyethanol; Ethylhexylglycerin | preservative | 0.6 | 0.6 | 0.6 | 0.6 | 0.6 |

TABLE 1-continued

Comparative Examples 1-5

| EU INCI Name | Function | Comparative Example 1 | Comparative Example 2 | Comparative Example 3 | Comparative Example 4 | Comparative Example 5 |
|---|---|---|---|---|---|---|
| Zea Mays Starch; Aqua | absorbant | 1 | 1 | 1 | 1 | 1 |
| Ethylhexylglycerin | help/boost preservation | 0 | 0 | 0 | 0 | 0 |
|  |  | 100 | 100 | 100 | 100 | 100 |
| Ratio A: Gelling agent/Emulsifier | | 1.00 | 7.00 | 1.00 | 0.14 | 1.00 |
| Ratio B: Gelling agent/Emollient | | 0.02 | N/A | N/A | N/A | 0.14 |
| Ratio C: Wax/Emollient | | 0.80 | N/A | N/A | N/A | 0.80 |
| pH | | 5.52 | 5.43 | 5.41 | 5.87 | 5.53 |
| Viscosity | | 434 | 10700 | 14.6 | 1240 | 14100 |
| Evacuation | | 90.1 | 40.4 | 93.3 | 76.6 | — |
| Firmness | | 1.2 | 6.8 | 0.1 | 2.7 | 8.6 |
| Slipperiness | | 5.2 | 3.3 | 8.9 | 6.8 | 4.7 |
| Braking | | 5.1 | 6.8 | 0.4 | 3.5 | 6.2 |

TABLE 2

Comparative Examples 6-11

| EU INCI Name | Function | Comparative Example 6 | Comparative Example 7 | Comparative Example 8 | Comparative Example 9 | Comparative Example 10 | Comparative Example 11 |
|---|---|---|---|---|---|---|---|
| Aqua | vehicle | 78.312 | 76.312 | 76.312 | 76.312 | 67.112 | 76.312 |
| Carbomer (Carbopol ® U10) | gelling agent | 0.2 | 0.2 | 1.4 | 1.4 | 1.4 | 0.2 |
| Potassium Cetyl Phosphate; Hydrogenated Palm Glycerides | emulsifier | 1.4 | 1.4 | 0.2 | 0.2 | 1.4 | 1.4 |
| Cetyl Alcohol | Emollient (Wax) | 8 | 0 | 0 | 0 | 8 | 0 |
| Cocoglycerides (Myritol ® 331) | emollient | 0 | 10 | 10 | 10 | 10 | 10 |
| Glycerin | humectant | 10 | 10 | 10 | 10 | 10 | 10 |
| Disodium EDTA | chelant | 0.15 | 0.15 | 0.15 | 0.15 | 0.15 | 0.15 |
| p-Anisic Acid | masking agent | 0.15 | 0.15 | 0.15 | 0.15 | 0.15 | 0.15 |
| Sodium Hydroxide | pH ajuster | 0.188 | 0.188 | 0.188 | 0.188 | 0.188 | 0.188 |
| Phenoxyethanol; Ethylhexylglycerin | preservative | 0.6 | 0.6 | 0.6 | 0.6 | 0.6 | 0.6 |
| Zea Mays Starch; Aqua | absorbant | 1 | 1 | 1 | 1 | 1 | 1 |
| Ethylhexylglycerin | help/boost preservation | 0 | 0 | 0 | 0 | 0 | 0 |
|  |  | 100 | 100 | 100 | 100 | 100 | 100 |
| Ratio A: Gelling agent/Emulsifier | | 0.14 | 0.14 | 7.00 | 7.00 | 1.00 | 0.14 |
| Ratio B: Gelling agent/Emollient | | NA | 0.02 | 0.14 | 0.14 | 0.14 | 0.02 |
| Ratio C: Wax/Emollient | | NA | 0.00 | 0.00 | 0.00 | 0.80 | 0.00 |
| PH | | 5.26 | 5.62 | 5.4 | 5.49 | 5.42 | 5.78 |
| Viscosity | | 1040 | 41.6 | 8530 | 7630 | 13200 | 58 |
| Evacuation | | 79.5 | 93.2 | 30.3 | 36.1 | 15.8 | 93.1 |
| Firmness | | 4.7 | 0.3 | 5.9 | 5.9 | 9 | 0.3 |
| Slipperiness | | 6.8 | 8.0 | 5.3 | 4.8 | 3.8 | 8.6 |
| Braking | | 4.1 | 0.9 | 4.7 | 5.6 | 6.6 | 1.8 |

TABLE 3

Comparative Examples 12-17

| EU INCI Name | Function | Comparative Example 12 | Comparative Example 13 | Comparative Example 14 | Comparative Example 15 | Comparative Example 16 | Comparative Example 17 |
|---|---|---|---|---|---|---|---|
| Aqua | vehicle | 85.112 | 85.112 | 87.512 | 78.312 | 69.512 | 77.312 |
| Carbomer | gelling agent | 1.4 | 1.4 | 0.2 | 1.4 | 0.2 | 0.8 |
| Potassium Cetyl Phosphate; Hydrogenated Palm Glycerides | emulsifier | 1.4 | 1.4 | 0.2 | 0.2 | 0.2 | 0.8 |
| Cetyl Alcohol | Emollient (Wax) | 0 | 0 | 0 | 8 | 8 | 4 |
| Cocoglycerides | emollient | 0 | 0 | 0 | 0 | 10 | 5 |
| Glycerin | humectant | 10 | 10 | 10 | 10 | 10 | 10 |
| Disodium EDTA | chelant | 0.15 | 0.15 | 0.15 | 0.15 | 0.15 | 0.15 |
| p-Anisic Acid | masking agent | 0.15 | 0.15 | 0.15 | 0.15 | 0.15 | 0.15 |
| Sodium Hydroxide | pH ajuster | 0.188 | 0.188 | 0.188 | 0.188 | 0.188 | 0.188 |
| Phenoxyethanol; Ethylhexylglycerin | preservative | 0.6 | 0.6 | 0.6 | 0.6 | 0.6 | 0.6 |
| Zea Mays Starch; Aqua | absorbant | 1 | 1 | 1 | 1 | 1 | 1 |
| Ethylhexylglycerin | help/boost preservation | 0 | 0 | 0 | 0 | 0 | 0 |
| | | 100 | 100 | 100 | 100 | 100 | 100 |
| Ratio A: Gelling agent/Emulsifier | | 1.00 | 1.00 | 1.00 | 7.00 | 1.00 | 1 |
| Ratio B: Gelling agent/Emollient | | NA | NA | NA | NA | 0.02 | 0.16 |
| Ratio C: Wax/Emollient | | NA | NA | NA | NA | 0.80 | 0.8 |
| pH | | 5.43 | 5.49 | 5.5 | 5.52 | 5.46 | 5.44 |
| Viscosity | | 6900 | 7730 | 18 | 12000 | 469 | 5650 |
| Evacuation | | 56.4 | 49.6 | 93.3 | 44.9 | 90.1 | |
| Firmness | | 6.2 | 5.3 | 0.1 | 7.9 | 1.5 | 7.1 |
| Slipperiness | | 4.9 | 5.4 | 7.9 | 3.1 | 5.2 | 5.3 |
| Braking | | 5.0 | 5.2 | 0.8 | 7.1 | 5.3 | 4.6 |

Working Examples According to the Present Invention

The compositions in Table 4 were prepared as set forth above. Measurements and observations were made on compositions Example 17 to Example 21 as set forth in the description below.

TABLE 4

Inventive Examples 18-22

| EU INCI Name | Function | Invention Example 18 | Invention Example 19 | Invention Example 20 | Invention Example 21 | Invention Example 22 |
|---|---|---|---|---|---|---|
| Aqua | Vehicle | 82.312 | 86.012 | 77.762 | 85.762 | 77.512 |
| Carbomer | gelling agent | 0.5 | 0.4 | 0.55 | 0.4 | 0.55 |
| Potassium Cetyl Phosphate; Hydrogenated Palm Glycerides | Emulsifier | 0.6 | 0.5 | 0.6 | 0.5 | 0.6 |
| Cetyl Alcohol | Emollient (Wax) | 1.5 | 2 | 3 | 2 | 3 |
| Cocoglycerides | Emollient | 3 | 4 | 6 | 4 | 6 |
| Glycerin | Humectant | 10 | 5 | 10 | 5 | 10 |
| Disodium EDTA | Chelant | 0.15 | 0.15 | 0.15 | 0.2 | 0.2 |
| p-Anisic Acid | masking agent | 0.15 | 0.15 | 0.15 | 0.15 | 0.15 |
| Sodium Hydroxide | pH ajuster | 0.188 | 0.188 | 0.188 | 0.188 | 0.188 |
| Phenoxyethanol; Ethylhexylglycerin | Preservative | 0.6 | 0.6 | 0.6 | 0.6 | 0.6 |
| Zea Mays Starch; Aqua | Absorbant | 1 | 1 | 1 | 1 | 1 |
| Ethylhexylglycerin | help/boost preservation | 0 | 0 | 0 | 0.2 | 0.2 |
| | | 100 | 100 | 100 | 100 | 100 |
| Ratio A: Gelling agent/Emulsifier | | 0.83 | 0.80 | 0.92 | 0.80 | 0.92 |
| Ratio B: Gelling agent/Emollient | | 0.17 | 0.10 | 0.09 | 0.10 | 0.09 |
| Ratio C: Wax/Emollient | | 0.50 | 0.50 | 0.50 | 0.50 | 0.50 |
| Viscosity | | 2440 | 1553 | 2947 | 1553 | 2947 |
| Evacuation | | N/A[1] | 83.9 | N/A | 83.9 | N/A |

TABLE 4-continued

Inventive Examples 18-22

| EU INCI Name | Function | Invention Example 18 | Invention Example 19 | Invention Example 20 | Invention Example 21 | Invention Example 22 |
|---|---|---|---|---|---|---|
| | Firmness | 3.0 | 2.1 | 3.3 | 2.1 | 3.3 |
| | Slipperiness | 9.1 | 9.3 | 9.0 | 9.3 | 9.0 |
| | Braking | 1.2 | 1.0 | 1.4 | 1.0 | 1.4 |

[1]N/A values for evacuation rate are due to the difference between cream and lotion. Evacuation rate is relevant only for lotions (packaging equipped with a pump).

Measurements and Observations
Slipperiness (Ratio A)

A sensory test can be employed to evaluate the creams and lotions prepared in accordance with the invention as set forth below.

The perceived skinfeel attribute of slipperiness of the inventive compositions can be evaluated using ten trained panelists. Each panelist should follow the protocol below:
1. Apply 0.07 mL on the back of the hand and spread it with 2 fingers (index and middle fingers).
2. Evaluate after 2 turns of application slipperiness during application.

The "slipperiness" during application of a composition is determined as to how the product feels to a panelist after two turns of application with the finger on the back of the hand. Each panelist notes the ease to move a finger across the surface of the hand. The scale is from 0 to 10; 0 being not slippery and 10 being highly slippery. A value of slipperiness acceptable for the consumer ranges from 6.5 to 9.5.

Referring to FIG. 1, the graph in FIG. 1 is based on the mean slipperiness values of comparatives examples 1 to 16; relatives to their Carbopol® U10 (gelling agent) and Emulsiphos® (emulsifier) content. For example, slipperiness for 0.2% Carbopol® U10 and 0.2% Emulsiphos® is the mean value of the slipperiness in comparative examples 1, 3, 14 and 16. The vertical axis represents the slipperiness value. The horizontal axis displays two types of compositions: on the left, compositions containing 0.2% of Carbopol® U10; and on the right, compositions containing 1.4% of Carbopol® U10. Circle points indicate value estimated for compositions containing 0.2% emulsifier (Emulsiphos®). Square points indicate value estimated for compositions containing 1.4% emulsifier (Emulsiphos®). The two points on the left of the graph represent the slipperiness for two compositions comprising a low content of gelling agent (0.2%); the square is a composition with a high content of emulsifier (1.4%), the circle is a composition with a low content of emulsifier (0.2%). The two points on the right of the graph represent the slipperiness for two compositions comprising a high content of gelling agent (1.4%); the square is a composition with a high content of emulsifier (1.4%), the circle is a composition with a low content of emulsifier (0.2%). The plain line is linking the dots representing the experiments with a low content of emulsifier (0.2%). The hashed line is linking the dots representing the experiments with a high content of emulsifier (1.4%). Surprisingly the two lines are crossing, while they should be somewhat parallel. The composition containing a high amount of gelling agent and low content of emulsifier (circle dot on the right side of the graph) is surprisingly low with respect to its equivalent with a high content of emulsifier. This means that contrary to what can be expected, for a composition containing a high amount of gelling agent, the slipperiness would be higher if the composition contains more emulsifying agent.

Evacuation Rate (Ratio B)

An evacuation rate should be at least about 82% to be acceptable for the consumer. This applies particularly to lotions due to the packaging used for this type of composition (for example bottle equipped with a pump). Evacuation rate is obtained from an automated compression test using a texture analyzer TA-XT.

Automated compression test is as follows: 300 cycles of pump actuation are performed by an automated system (texture analyzer TA-XT). Automated system moves up and down the pump mechanism at a 10 mm/sec speed, over a 17 mm course. Evacuation rate is calculated as the variation of mass of product in a 250 ml packaging, expressed in percentage, between the initial mass (before the 300 cycles) and the final mass (after the 300 cycles). A 100% evacuation rate means that all of the product has been recovered from the packaging; wherein a 50% evacuation rate means that half of the product has been recovered.

Figure 2:
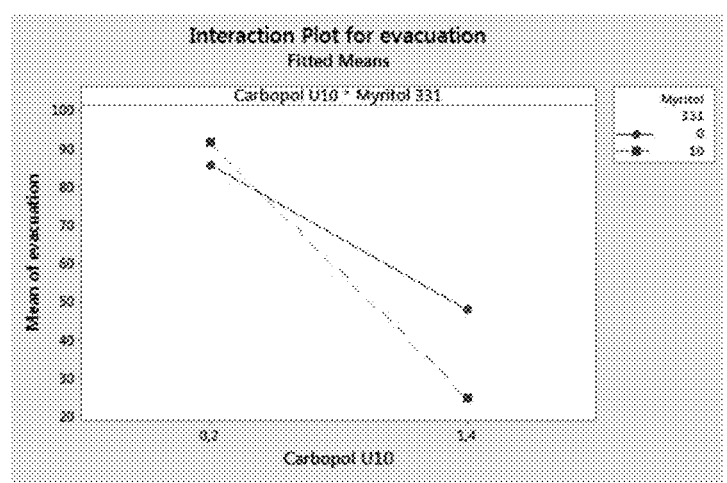
FIG. 2 is a graph showing mean evacuation rate relative to amount of gelling agent and amount of emollient.

Referring to FIG. 2, FIG. 2 is a graph that shows the mean evacuation rate values of comparatives examples 1 to 16; relatives to their Carbopol® U10 (gelling agent) and Myritol® 331 (emollient) content. For example, the value of the evacuation rate for 0.2% Carbopol® U10 and 10% Myritol® 331 is the mean value of the evacuation rate for examples 1, 7, 11 and 16. The vertical axis represents the evacuation rate value, 100 means that all of the product was recovered from the packaging; and in contrast, 20 means that only 20% of the product was recovered. The horizontal axis displays two types of compositions: on the left, compositions containing 0.2% of Carbopol® U10; and on the right, compositions containing 1.4% of Carbopol® U10. Square points indicate values estimated for composition containing 10% emollient (Cocoglyceride); Circle points indicate values for compositions containing no emollient. The two points on the left of the graph represent the evacuation rates for two compositions comprising a low content of gelling agent (0.2%); the square is a composition with an emollient (10%), the circle is a composition without emollient. The two points on the right of the graph represent the evacuation rates for two compositions comprising a high content of gelling agent (1.4%); the square is a composition with an emollient (10%), the circle is a composition without emollient. The plain line is linking the dots representing the experiments without emollient. The hashed line is linking the dots representing the experiments with 10% emollient. Surprisingly the two lines are crossing, while they should be somewhat parallel. The composition containing a low amount of gelling agent and an emollient (square dot on the left side of the graph) is surprisingly high with respect to its equivalent without an emollient. This means that contrary to what can be expected, for a composition containing a low amount of gelling agent, the evacuation rate would be better if the composition contains an emollient.

Braking and Firmness

A sensory panel has been performed on Examples 1-17 in accordance with the methodology set forth below. The same methodology can be employed to evaluate the inventive creams and lotions of Examples 18-22.

Sensorial Test—Braking on Application Attribute Protocol:

Apply 0.07 mL on the back of the hand and spread it with 2 fingers (index and middle fingers). Measure the speed of apparition of a braking effect (dragging) while spreading the product on the skin (in total 20 turns on the back of the hand is apply). This test is to be performed by 10 trained panel. The panel is to note the number of turns they make until braking effect (dragging) is observed. Scale is from 0 to 10 (0 very draggy and 10 not draggy). A value of baking acceptable for the consumer range from 1 to 5.

Sensorial Test—Firmness Attribute Protocol:

Open the product which is in a jar. Evaluate the resistance of the product when introducing the index finger in the jar. This test is to be performed by 10 trained panel. Scale is from 0 to 10 (0 not firm (i.e. water) and 10 very firm (i.e. jelly)). A value of firmness acceptable for the consumer range from 1.5 to 5.

Viscosity

A value of viscosity acceptable for the consumer ranges from 950 mPa 1600 mPas for lotions and 1400-4800 mPa for creams. Viscosities can be measured using a rheometer, Anton Paar MCR 301, with the following protocol:
1. Set-up at 20° C. during 120 s. No shear rate.
2. 3 measures every 10 sec at 5 s$^{-1}$
3. 9 measures every 4 sec during increase from 5 s$^{-1}$ to 45 s$^{-1}$
4. 2 measures every 5 sec at 45 s$^{-1}$
5. The value to be recorded for viscosity is the 2nd measure at 45 s$^{-1}$ Based on the measurements and sensory panel discussed above, personal care composition appearance for inventive Examples 18-22 can be observed as set forth in Table 5 below:

TABLE 5

| Composition | Product visual appearance is acceptable? | Aspect |
|---|---|---|
| Example 1 | No | Very liquid with grains |
| Example 2 | Yes | Thick and mat emulsion |
| Example 3 | No | Phase separation, sedimentation |
| Example 4 | No | Translucent, grains |
| Example 5 | No | Thick with a lot of grains |
| Example 6 | No | Grains from Cetyl Alcohol |
| Example 7 | No | Phase separation |
| Example 8 | Yes | White smooth and thick emulsion |
| Example 9 | No | Grains from Carbopol ® U10 |
| Example 10 | No | White and thick emulsion with a lot of grains |
| Example 11 | No | Phase separation |
| Example 12 | Yes | Translucent gel |
| Example 13 | Yes | Thick translucent gel |
| Example 14 | No | Phase separation, sedimentation |
| Example 15 | No | White and thick emulsion with a lot of grains |
| Example 16 | No | Very liquid with grains |
| Example 17 | Yes | Thick and mat emulsion |
| Example 18 (invention) | Yes | White smooth and thick emulsion (Thick to achieve a Cream texture) |

TABLE 5-continued

| Composition | Product visual appearance is acceptable? | Aspect |
|---|---|---|
| Example 19 (invention) | Yes | White smooth and fluid emulsion (fluid to achieve a Lotion texture) |
| Example 20 (invention) | Yes | White smooth and thick emulsion (Thick to achieve a Cream texture) |
| Example 21 (invention) | Yes | White smooth and thick emulsion (Thick to achieve a Cream texture) |
| Example 22 (invention) | Yes | White smooth and fluid emulsion (fluid to achieve a Lotion texture) |

What is claimed is:

1. A personal care composition consisting of:
   from about 3 wt. % based on the total weight of the personal care composition to about 6 wt. % based on the total weight of the personal care composition of an emollient, wherein the emollient is cocoglyceride;
   from about 1.5 wt. % based on the total weight of the personal care composition to about 3 wt. % based on the total weight of the personal care composition of an emollient wax;
   an emulsifier, wherein the emulsifier is cetyl phosphate;
   a gelling agent; and
   water;
   wherein the personal care composition consists of the ingredients in the following ratios:
   a) the ratio between the gelling agent and the emulsifier ranges from 1 to 0.5;
   b) the ratio between the gelling agent and the emollient ranges from 1 to 0.02; and
   c) the ratio between the emollient wax and the emollient is less than or equal to 0.5.

2. The personal care composition of claim 1, wherein the emollient wax is cetyl alcohol.

3. The personal care composition of claim 1, wherein the gelling agent is a carbomer.

4. The personal care composition of claim 1, wherein the emulsifier is present in the amount of from about 0.2 wt. % based on the total weight of the personal care composition to about 1.4 wt. % based on the total weight of the personal care composition.

5. The personal care composition of claim 1, wherein the gelling agent is present in the amount of from about 0.4 wt. % based on the total weight of the personal care composition to about 0.64 wt. % based on the total weight of the personal care composition.

6. The personal care composition of claim 1, wherein the emulsifier is present in the amount of from about 0.4 wt. % based on the total weight of the personal care composition to about 1.4 wt. % based on the total weight of the personal care composition.

7. The personal care composition of claim 1, wherein the emulsifier is present in the amount of from about 0.5 wt. % based on the total weight of the personal care composition to about 0.6 wt. % based on the total weight of the personal care composition.

8. The personal care composition of claim 1, wherein the gelling agent is present in the amount of from about from about 0.4 wt. % based on the total weight of the personal care composition to about 0.5% wt. % based on the total weight of the personal care composition.

* * * * *

UNITED STATES PATENT AND TRADEMARK OFFICE
CERTIFICATE OF CORRECTION

| | |
|---|---|
| PATENT NO. | : 11,464,723 B2 |
| APPLICATION NO. | : 16/411553 |
| DATED | : October 11, 2022 |
| INVENTOR(S) | : Hortense Baillet et al. |

It is certified that error appears in the above-identified patent and that said Letters Patent is hereby corrected as shown below:

In the Claims

Column 14, Claim 1, Line 33 should read:
-c) the ratio between the wax and the emollient- Column 14, Claim 5, Line 47 should read:
-to about 0.6 wt. % based on the total weight of the personal- Signed and Sealed this
Nineteenth Day of September, 2023

Katherine Kelly Vidal
*Director of the United States Patent and Trademark Office*